(12) United States Patent
Choi et al.

(10) Patent No.: US 7,727,159 B2
(45) Date of Patent: Jun. 1, 2010

(54) APPARATUS AND METHOD FOR DETECTING BLOOD FLOW SIGNAL FREE FROM MOTION ARTIFACT AND STRESS TEST APPARATUS USING THE SAME

(75) Inventors: Ki-wan Choi, Anyang-si (KR);
Hyoung-ki Lee, Suwon-si (KR);
Seok-won Bang, Seoul (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 1579 days.

(21) Appl. No.: 10/909,305

(22) Filed: Aug. 3, 2004

(65) Prior Publication Data
US 2005/0038349 A1    Feb. 17, 2005

(30) Foreign Application Priority Data
Aug. 11, 2003    (KR)    ............. 10-2003-0055537

(51) Int. Cl.
*A61B 5/02*    (2006.01)
(52) U.S. Cl. .................. 600/504; 600/481
(58) Field of Classification Search ............ 600/504
See application file for complete search history.

(56) References Cited

U.S. PATENT DOCUMENTS

| | | | |
|---|---|---|---|
| 3,139,086 | A | 6/1964 | Botsch et al. |
| 4,478,224 | A | 10/1984 | Bailey |
| 4,692,034 | A | 9/1987 | Fukui et al. |
| 5,119,450 | A | 6/1992 | Ranganath et al. |
| 5,653,239 | A | 8/1997 | Malecki et al. |
| 5,662,106 | A | 9/1997 | Swedlow et al. |
| 5,876,350 | A | 3/1999 | Lo et al. |
| 5,899,855 | A | 5/1999 | Brown |
| 6,491,639 | B1 | 12/2002 | Turcott |
| 6,896,661 | B2 * | 5/2005 | Dekker .......... 600/529 |

(Continued)

FOREIGN PATENT DOCUMENTS

EP    1 327 413 A2    7/2003

(Continued)

OTHER PUBLICATIONS

European Search Report issued Mar. 2, 2005.

(Continued)

*Primary Examiner*—Patricia C Mallari
(74) *Attorney, Agent, or Firm*—Staas & Halsey LLP

(57) ABSTRACT

An apparatus and method to detect a blood flow signal free from a motion artifact, and a stress test apparatus using the same, enhance data reliability of the blood flow signal by removing the motion artifact from the blood flow signal detected by photo-plethysmography. The apparatus to detect the blood flow signal includes a base pattern correlation coefficient calculating unit to determine peak points in the blood flow signal sensed from a body of an examinee using a blood flow sensing unit, and to calculate correlation coefficients of each peak point using a predetermined base pattern, and a motion artifact processing unit to determine the motion artifact using the calculated correlation coefficients and to remove the motion artifact from the blood flow signal. Thus, reliability of the blood flow signal is enhanced by effectively removing the motion artifact from the blood flow signal detected by the photo-plethysmography.

41 Claims, 10 Drawing Sheets

U.S. PATENT DOCUMENTS

2002/0045835 A1     4/2002    Masakov et al.
2003/0225337 A1*   12/2003   Scharf et al. ................ 600/508

FOREIGN PATENT DOCUMENTS

| | | |
|---|---|---|
| EP | 1 327 413 A3 | 12/2003 |
| JP | 05-184548 | 7/1993 |
| JP | 11-019056 | 1/1999 |
| JP | 11-155826 | 6/1999 |
| JP | 11-332837 | 12/1999 |
| JP | 2002-330934 | 11/2002 |
| JP | 2003-61921 | 3/2003 |
| KR | 10-2002-0005110 | 1/2002 |
| KR | 10-2003-0081903 | 10/2003 |
| KR | 10-2004-0067240 | 7/2004 |
| WO | WO 02/053024 | 7/2002 |

OTHER PUBLICATIONS

International Search Report issued Sep. 4, 2002.
Notice of Examination Report issued Aug. 16, 2005 in connection with Korean patent application 2003-0055537.
European Search Report for corresponding European Patent Application No. 04254811.5 dated Mar. 12, 2008, 5 pgs (in English).

* cited by examiner

APPARATUS AND METHOD FOR DETECTING BLOOD FLOW SIGNAL FREE FROM MOTION ARTIFACT AND STRESS TEST APPARATUS USING THE SAME

CROSS-REFERENCE TO RELATED APPLICATIONS

This application claims the priority of Korean Patent Application No. 2003-0055537 filed on Aug. 11, 2003, in the Korean Intellectual Property Office, the disclosure of which is incorporated herein in its entirety by reference.

BACKGROUND OF THE INVENTION

1. Field of the Invention

The present invention relates to an apparatus and method to detect a blood flow signal free from a motion artifact as well as a stress test apparatus using the same, in which the motion artifact caused by the motion of an examinee is removed from the blood flow signal detected by photo-plethysmography using a predetermined base pattern, thus performing exact detection of the blood flow signal as well as exact stress measurement using heartbeat information calculated through the detection.

2. Description of the Related Art

Generally, photo-plethysmography (hereinafter, referred to as "PPG") is used to detect a blood flow signal associated with a heartbeat by use of a predetermined number of LEDs (Light Emitting Diodes) and photo-detectors, for example, to extract blood flow information through a contact point at which a simple sensor module is in contact with a part of a human body (e.g., a finger or an ear).

The PPG has been widely used in test equipment to check a state of an examinee with or without a medical purpose, because the examinee may be easily examined compared to a heartbeat-detection test using an electrocardiogram (ECG), where two or more electrodes must be attached to the examinee.

Specifically, a representative example of the PPG is a stress test, in which a heart rate (referred to as HR hereinafter) and a heart rate variability (referred to as HRV hereinafter) are calculated using the blood flow signal obtained through the PPG, and then a stress level is measured by information on mental and/or physical states of the examinee, which is obtained through analysis of the HR and HRV.

Meanwhile, the PPG has a drawback in that even slight motion of the examinee brings about a noticeable motion artifact. The motion artifact is a noise signal caused by shaking or vibration of the examinee during detecting the blood flow signal, acting as a serious obstacle to exact detection of the HR and HRV.

There has been a proposal to overcome the drawback in U.S. Pat. No. 5,662,106, titled OXIMETER WITH MOTION DETECTION FOR ALARM MODIFICATION, in which a predetermined threshold value, which is obtained through a waveform of a derivative signal resulted from motion of an examinee, is set, and when a motion artifact is checked, an alarm is given to the examinee.

Specifically, as shown in FIG. 1, a ratio of the height of the positive peak of the derivative signal, A, and the height of the negative peak of the derivative signal, B, is greater than 1-1.4 for the blood flow pulse signal. Accordingly, a threshold value is set to 1-1.4, and signals having values less than the threshold value are determined to be the motion artifacts.

This method has a problem in that, during operation of a timer for a predetermined time and detecting a blood flow signal through a part of the body of the examinee, if it is determined that signals caused by the motion artifact are present, the timer is reset, and then the blood flow signal must be detected again. Thus, the whole measurement time is increased, causing a burden with respect to the detection of the blood flow signal.

Further, emission of an alarm sound indicating the presence of the motion artifact may cause the examinee to have a hesitating or shaking motion. Hence, the method does not function as an effective one for exact detection of the blood flow signal from which the motion artifact is removed.

For this reason, there is a need for an effective method to detect blood flow which is capable of providing exact information on the heartbeat and stress by more rapid and exact detection of the blood flow signal without imposing a burden on the examinee.

SUMMARY OF THE INVENTION

To solve the above and/or other problems, it is, therefore, an aspect of the invention to enhance data reliability of a blood flow signal by removing a motion artifact from the blood flow signal detected by photo-plethysmography.

It is another aspect of the invention to calculate the exact heart rate (HR) and the heart rate variability (HRV), using a blood flow signal from which a motion artifact is removed, to check a stress level of an examinee using the calculated HR and HRV, and to provide the examinee with an exact result of checking the stress level.

To achieve these and/or other aspects, in an embodiment of the invention, an apparatus to detect a blood flow signal free from a motion artifact comprises a base pattern correlation coefficient calculating unit to determine peak points in the blood flow signal sensed from the body of an examinee by a blood flow sensing means, and to calculate correlation coefficients of each peak point using a predetermined base pattern, and a motion artifact processing unit to determine the motion artifact using the calculated correlation coefficients and remove the motion artifact from the blood flow signal.

Consistent with another aspect of the invention, a method detects a blood flow signal free from a motion artifact, the method comprising detecting the blood flow signal sensed from a body of an examinee utilizing a blood flow sensing unit, determining peak points in the calculated blood flow signal and calculating correlation coefficients of each peak point using a predetermined base pattern, and determining the motion artifact using the calculated correlation coefficients and removing the motion artifact from the blood flow signal.

Consistent with yet another aspect of the invention, a stress test apparatus has an apparatus to detect a blood flow signal free from a motion artifact, the apparatus comprising a motion artifact removing section to remove the motion artifact caused by an examinee from the blood flow signal detected from a body of the examinee sensed through a blood flow sensing unit, a heartbeat information calculating section to calculate heartbeat information using the blood flow signal from which the motion artifact is removed utilizing the motion artifact removing section, and a stress testing section to calculate a stress index using the heartbeat information calculated utilizing the heartbeat information calculating section and checking the physical state of the examinee.

Here, the stress test apparatus may further comprise a display section to provide information on the physical state of the examinee obtained utilizing the stress testing section on a Graphic User Interface (GUI) screen, and a storage section to store information on the physical state of the examinee and information on a suitable prescription according to the physical state of the examinee.

The invention utilizes the predetermined base pattern obtained through a pure blood flow signal from which a motion artifact is removed. Correlation coefficients $C_i$ at each peak point of the blood flow signal are compared with the predetermined threshold value, wherein the correlation coefficients $C_i$ are calculated by correlation analysis using the base pattern. The motion artifact is determined by a result of the comparison and is removed from the blood flow signal.

Furthermore, the base pattern is extracted from a predetermined area of the blood flow signal where the pure blood flow signal measured under a test environment free from the motion artifact is determined to be optimal.

In addition, the threshold value is a value set to determine whether the motion artifact is present by using the correlation coefficients, in which the value is set to approximately 0.8, which has been determined to be optimal when the threshold value was tested in a range from 0.7 to 0.9.

Hereinafter, with regard to the apparatus and the method to detect a blood flow signal free from a motion artifact, as well as the stress test apparatus using the same in accordance with the present invention, an example in which the apparatus and method are realized by use of photo-plethysmography (PPG) corresponding to an exemplary example of the method to detect the blood flow signal is set forth below, but the example is simply illustrative. Therefore, those skilled in the art will understand that within the scope and spirit of the present invention, many variations and their equivalent modifications of the method may be implemented for removing the motion artifact from the blood flow signal by using the method to detect the blood flow signal by utilizing either the PPG or the mechanism to detect the blood flow signal through a contact point with a part of the human body.

Therefore, the scope of the technical protection of the present invention is set forth within the attached claims.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE PREFERRED EMBODIMENTS

Figure 1:
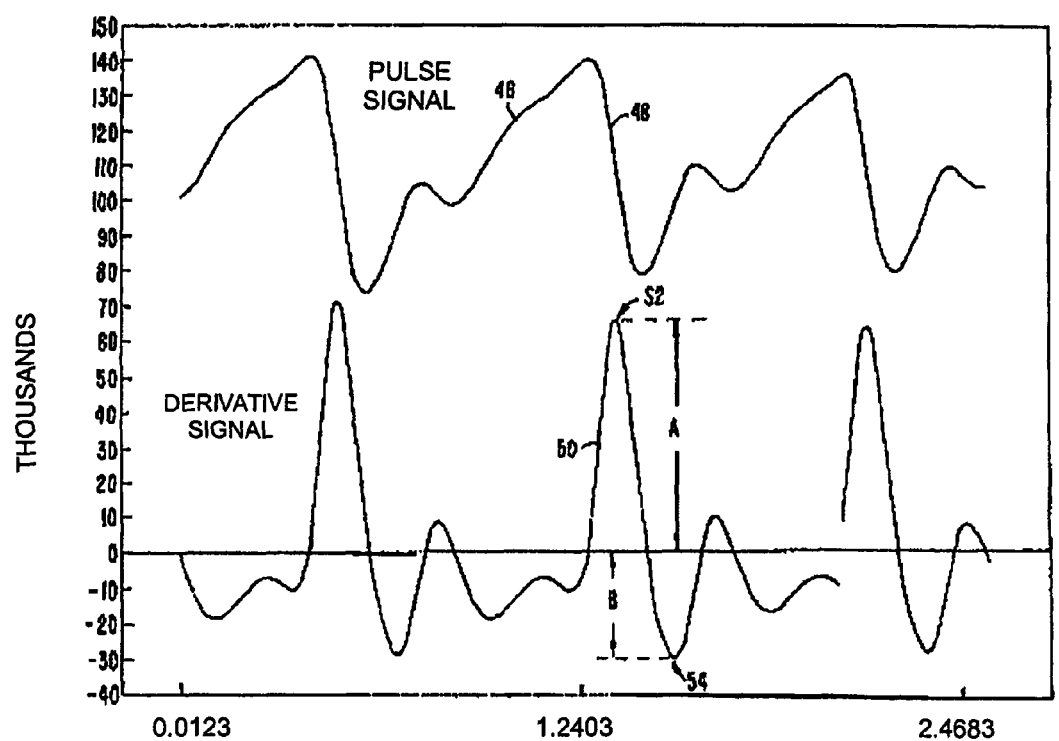
FIG. 1 shows waveforms of a derivative signal conventionally utilized to determine a motion artifact.

Reference will now be made in detail to the embodiments of the present invention, examples of which are illustrated in the accompanying drawings, wherein like reference numerals refer to the like elements throughout. The embodiments are described below to explain the present invention by referring to the figures.

Figure 2:
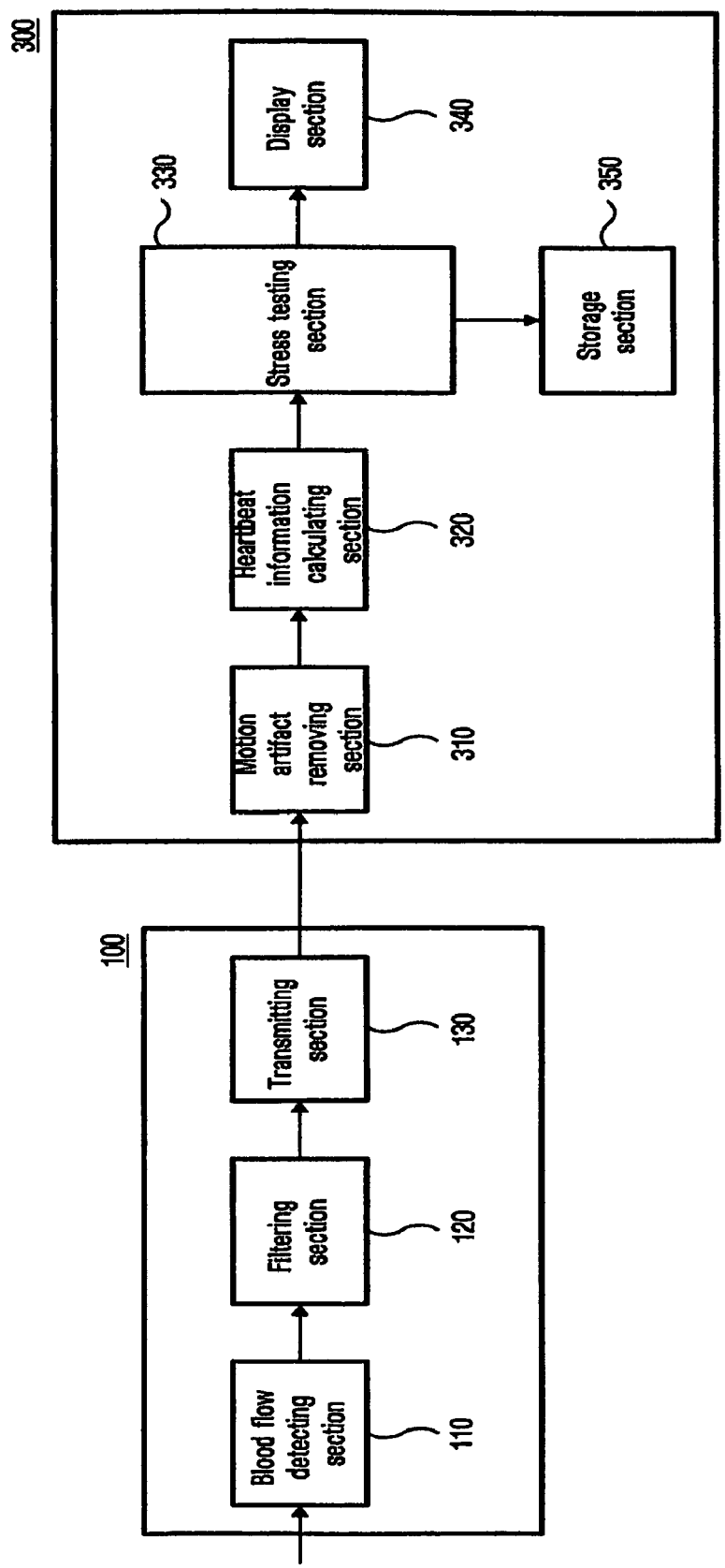
FIG. 2 is a schematic block diagram showing a configuration of a stress test apparatus using an apparatus to detect a blood flow signal free from a motion artifact in accordance with an embodiment of the present invention.

FIG. 2 is a schematic block diagram showing a configuration of a stress test apparatus using an apparatus to detect a blood flow signal free from a motion artifact in accordance with an embodiment of the present invention.

As shown in FIG. 2, an embodiment of the invention comprises a blood flow sensing apparatus 100 and a motion artifact removal and stress test apparatus 300. The embodiment of the invention further comprises a communication cable to transmit/receive signals between the blood flow sensing apparatus 100 and the motion artifact removal and stress test apparatus 300, wherein the communication cable has a specification of a predetermined interface (e.g., RA232C interface).

The blood flow sensing apparatus 100 comprises a blood flow detecting section 110 to detect a blood flow signal sensed through a contact point contacted with a part of the body of an examinee, a filtering section 120 to pass only waveforms of a particular frequency band in the blood flow signal detected at the blood flow detecting section 110, and a transmitting section 130 to transmit the filtered blood flow signal to the motion artifact removal and stress test apparatus 300 after processing the blood flow signal to be suitable for transmission.

The motion artifact removal and stress test apparatus 300 comprises a motion artifact removing section 310 to remove a motion artifact from the blood flow signal detected by the blood flow sensing apparatus 100, a heartbeat information calculating section 320 to calculate heartbeat information using the blood flow signal from which the motion artifact is removed, a stress testing section 330 to determine a physical state of the examinee using the heartbeat information calculated through the heartbeat information calculating section 320, a display section 340 to provide information on the physical state of the examinee obtained through the stress testing section 330 and the heartbeat information calculating section 320 on a Graphic User Interface (GUI) screen, and a storage section 350 to store the information with respect to the physical state according to the selection of the examinee.

Further, the storage section 350 stores prescription information provided according to the physical state of each examinee, and the stress testing section 330 transmits the prescription information suitable for each examinee, according to a result of testing, to the display section 340 together with the result of testing.

For example, the stress testing section 330 performs stress analysis using the heartbeat information calculated through the heartbeat information calculating section 320, searches for exercise cures, dietetic therapies or living information suitable for the physical state of the examinee according to the mental and/or physical stress indexes obtained as a result of the stress analysis at the storage section 350, and provides the searched result to the display section 340.

Figure 3:
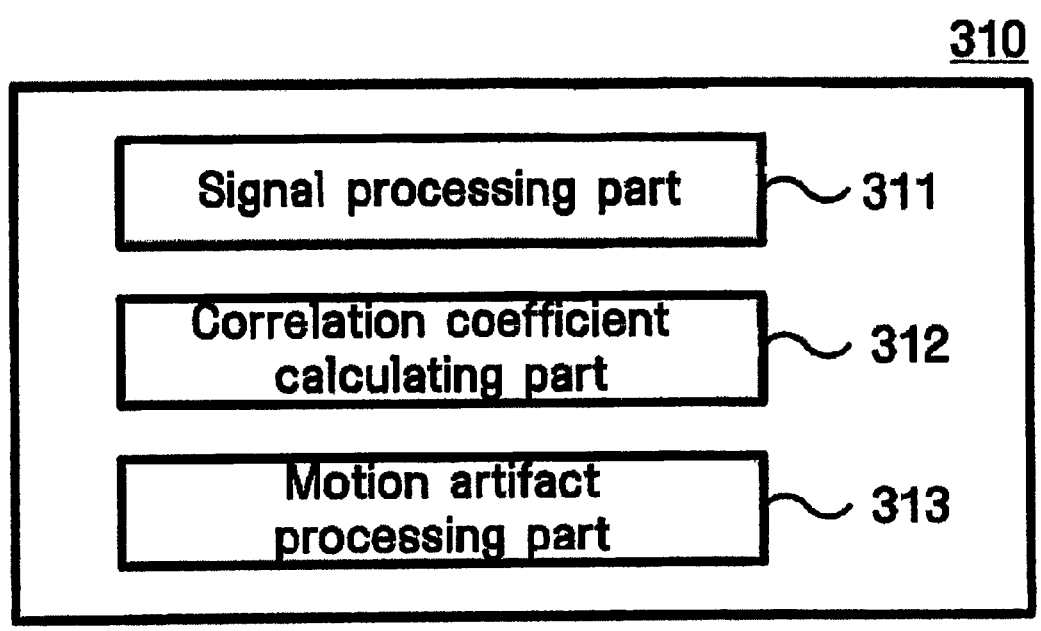
FIG. 3 is a schematic view showing a configuration of the motion artifact removing section of FIG. 2 in accordance with an embodiment of the present invention.

FIG. 3 is a schematic view showing a configuration of the motion artifact removing section of FIG. 2 in accordance with an embodiment of the invention.

As shown in FIG. 3, the motion artifact removing section 310 includes a signal processing part 311, a correlation coefficient calculating part, and a motion artifact processing part 313.

The signal processing part 311 pre-processes the blood flow signal detected through the blood flow sensing apparatus 100 to remove the motion artifact, and comprises normalizing, zero-clipping and smoothing procedures.

The normalizing procedure removes insignificant and unnecessary information, for example, DC components, by subtracting the overall mean value from each value of the detected blood flow signal, thus expressing the blood flow signal in an optimal state.

The zero-clipping procedure inverts a phase of the normalized blood flow signal to get exact peak points on a negative domain to remove the motion artifact, and truncates values less than zero on a positive domain.

The smoothing procedure smoothes the waveform of the blood flow signal, whose outline is roughened through the normalizing and zero-clipping procedures.

The correlation coefficient calculating part 312 determines the peak points of the blood flow signal processed through the signal processing part 311, and calculates correlation coefficients $C_i$ at each peak point using the following Equation 1.

$$C_i = \frac{\sum_{n=0}^{N}(x_{k(i,n)} - \bar{x})(b_n - \bar{b})}{\sqrt{\sum_{n=0}^{N}(x_{k(i,n)} - \bar{x})^2 \sum_{n=0}^{N}(b_n - \bar{b})^2}} \quad \text{EQUATION 1}$$

$$k(i, n) = \frac{(N-n)P_i + nP_{i+1}}{N}$$

where $x_n$ is an $n^{th}$ point of the blood flow signal,
$b_n$, is an $n^{th}$ point of the base pattern,
$k(i,n))$ is an $n^{th}$ point position from the $i^{th}$ peak,
$P_i$ is a $i^{th}$ peak point, and
N is the number of the base pattern signal,
i and n being integers.

Equation 1 is used to analyze a degree of correlation with a predetermined base pattern at a predetermined peak point, in which the base pattern is to extract a predetermined area of the blood flow signal where the pure blood flow signal measured under a test environment free from the motion artifact is determined to be optimal.

The motion artifact processing part 313 compares each correlation coefficient $C_i$, which is calculated through the correlation coefficient calculating part 312, with a predetermined threshold value, determines the motion artifact through a result of the comparison, and removes the motion artifact from the blood flow signals.

The predetermined threshold value is set to a value of, 0.8, which has been determined to be optimal when the threshold value was tested in a range between 0.7 and 0.9. For example, when the threshold value is set to be slightly lower than 0.8, it is possible to prevent the essential blood flow signal from being removed, even though the motion artifact is less filtered. However, if the threshold value is set slightly higher, the result is contrary.

When any correlation coefficient $C_i$ calculated through the correlation coefficient calculating part 312 is less than the threshold value, the motion artifact processing part 313 determines that the peak points are the motion artifacts and removes the peak points. On the other hand, when the correlation coefficient $C_i$ is greater than the threshold value, the motion artifact processing part 313 determines that the peak points represent the blood flow signal.

Figure 4:
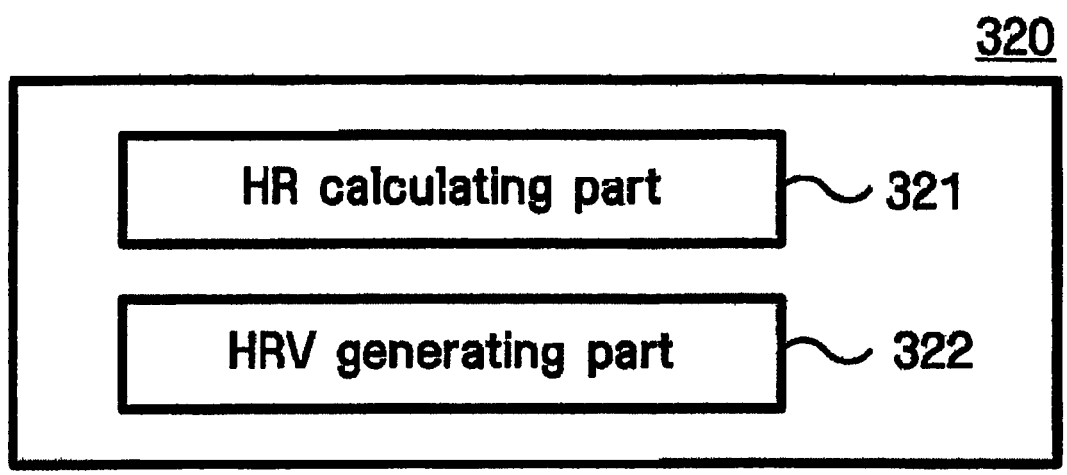
FIG. 4 is a schematic block diagram showing a configuration of the heartbeat information calculating section of FIG. 2 in accordance with an embodiment of the present invention.

FIG. 4 is a schematic block diagram showing a configuration of the heartbeat information calculating section of FIG. 2 in accordance with an embodiment of the invention.

As shown in FIG. 4, the heartbeat information calculating section 320 comprises a heart rate (HR) calculating part 321 and a heart rate variability (HRV) generating part 322.

The HR calculating part 321 calculates an interval $\Delta RR$ between the peak points, each of which is determined to be the blood flow signal through the motion artifact processing part 313 of the motion artifact removing section 310, and determines whether the interval $\Delta RR$ between the peak points is within the range of ±40% as a reference of HR.

As a result of the determination, if the interval $\Delta RR$ is within the range of ±40%, HR is calculated by dividing the interval $\Delta RR$ by 60. If the interval $\Delta RR$ is not within a range of ±40%, current peak points are determined to be motion artifacts and are excluded.

Further, the HR calculating part 321 determines whether the calculated HR is within the range from 40 to 150 with respect to the HR range of the human body, and as a result of the determination, if the calculated HR is within the HR range of the human body, current peak points are either determined to be the blood flow signal, or determined to be motion artifacts and are excluded.

The HRV generating part 322 allows the procedure of removing the motion artifacts using the motion artifact removing section 310 and the HR calculating part 321 to be performed with respect to all peak points of the blood flow signal detected from the blood flow sensing apparatus 100, and generates the HRV by collecting each peak point which is determined to be the blood flow signal.

Figure 5:
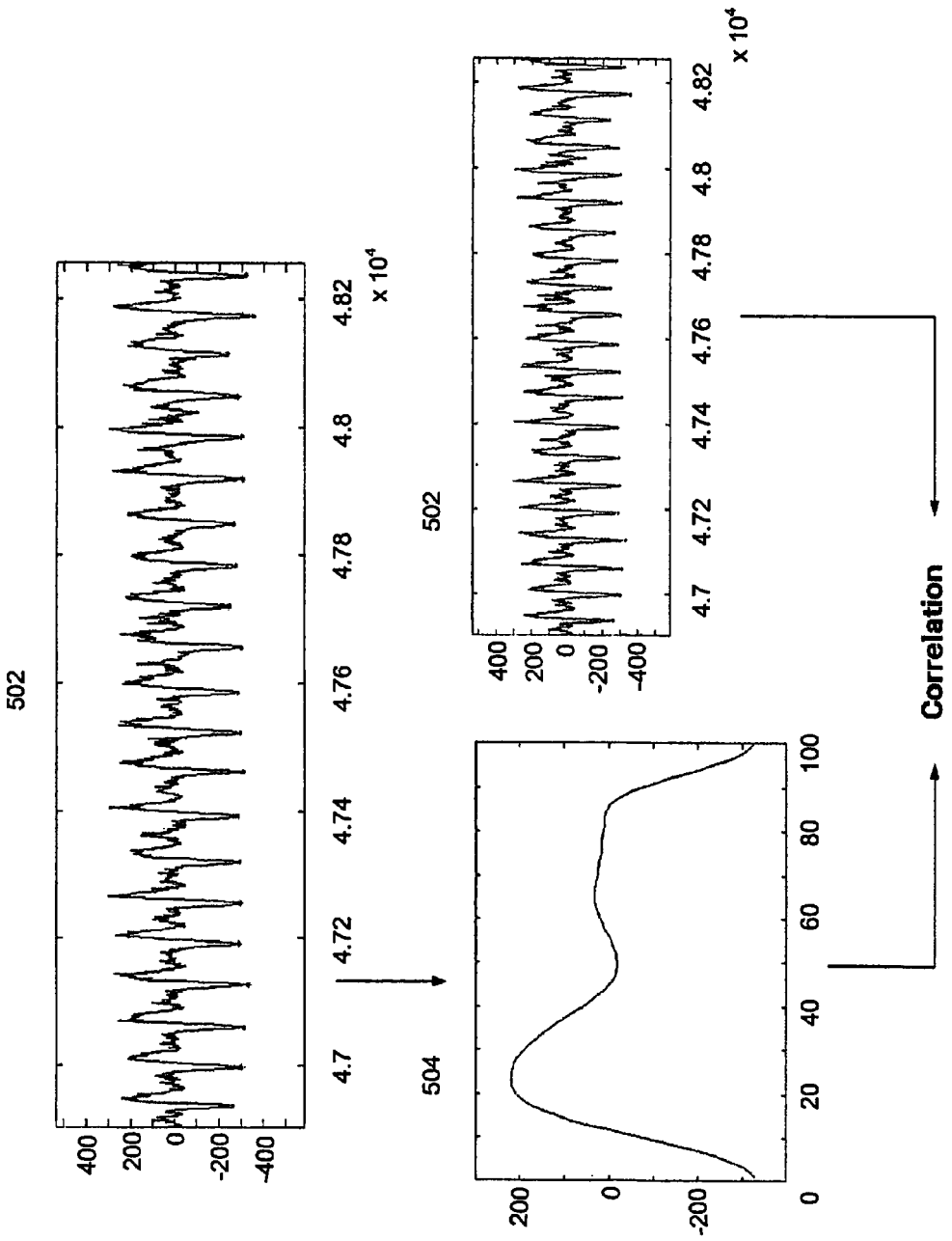
FIG. 5 shows procedures of extracting a base pattern and calculating a threshold value in accordance with an embodiment of the present invention.

FIG. 5 shows procedures of extracting a base pattern and calculating a threshold value in accordance with an embodiment of the invention.

As shown in FIG. 5, after establishing a test environment under which no motion artifact is generated, a pure blood flow signal (502) from which the motion artifact is removed is detected.

Then, a predetermined area of the blood flow signal where the detected blood flow signal is determined to be optimal is extracted and utilized as a base pattern (504) to determine the motion artifact.

It should be noted that the foregoing apparatus to detect blood flow signals free from motion artifacts and the foregoing stress test apparatus using the same may be constructed completely using hardware, using only software, or using both hardware and software.

Therefore, it will be apparent to those skilled in the art that the foregoing apparatuses according to the present invention may be not only implemented in hardware and/or software without departing from the spirit and scope of the invention, but also their modification and variation may be added by implementing them in hardware and/or software.

Hereinafter, a method to detect blood flow signals free from motion artifacts by use of the apparatus according to the invention and a stress test method using the same method will be described in detail with reference to the accompanying drawings.

Figure 6:
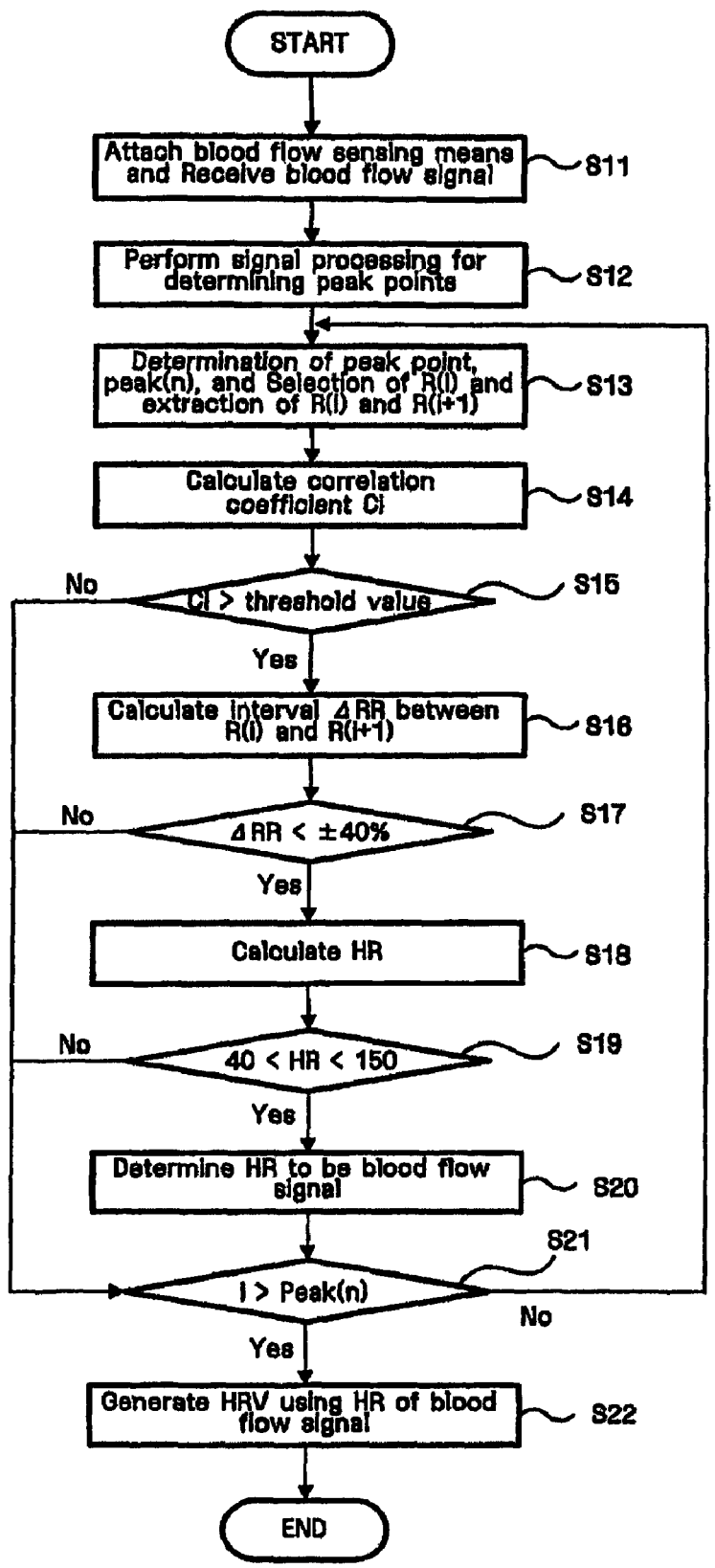
FIG. 6 is a schematic flow chart showing a procedure to detect a blood flow signal free from a motion artifact in accordance with an embodiment of the present invention.

FIG. 6 is a schematic flow chart showing a procedure to detect a blood flow signal free from a motion artifact in accordance with an embodiment of the invention.

As shown in FIG. 6, the motion artifact removing section 310 of the motion artifact removal and stress test apparatus 300 receives a blood flow signal detected through the blood flow sensing apparatus 100 when an examinee attaches the blood flow sensing apparatus 100 to a part of her/his body to perform a stress test (S11).

When the blood flow signal is received, the motion artifact removing section 310 processes the received blood flow signal to remove the motion artifact (S12), and determine peak points.

In the procedure of determining the peak points, if the peak points of the blood flow signal are determined to be an "n" number, peak(n), the $1^{st}$ to $i^{th}$ peak points R(1) to R(i) are sequentially selected, and then values of peak points R(i) and R(i+1) are extracted (S13).

Subsequently, the motion artifact removing section 310 calculates a correlation coefficient $C_i$ within a selected period between R(i) and R(i+1) using Equation 1 (S14), and determines whether the calculated correlation coefficient $C_i$ exceeds a predetermined threshold value (S15).

As a result of the determination, if the calculated correlation coefficient $C_i$ exceeds the predetermined threshold value, the peak points are determined to be the blood flow signal, and then the heartbeat information calculating section 320 calculates an interval ΔRR between the peak points R(i) and R(i+1) (S16).

Next, the heartbeat information calculating section 320 determines whether the interval ΔRR is within the range of a heartbeat reference (±40%) using the calculated interval ΔRR (S17).

As a result of the determination, if the calculated interval ΔRR is within the range of the heartbeat reference (±40%), an HR is calculated (S18), and it is determined whether the calculated HR is within the range from 40 to 150, i.e., the HR range of the human body (S19).

As a result of the determination, if the calculated HR is within the range from 40 to 150, the peak point R(i) which is presently selected is determined to be the blood flow signal (S20).

In this manner, when the presently selected period between the peak points R(i) and R(i+1) is either determined to be the blood flow signal, or determined and excluded due to being the motion artifact in the procedure of determining the motion artifact using the correlation coefficients $C_i$, the interval ΔRR and the HR, the heartbeat information calculating section 320 determines whether the current peak point is an $n^{th}$ peak point of the blood flow signal (S21).

As a result of the determination, if the current peak point R(i) is not the $n^{th}$ peak point of the blood flow signal, the next peak point R(i+1) is selected and then there is a return to the routine of removing the motion artifact and calculating the heartbeat information. However, if the current peak point R(i) is the $n_{th}$ peak point of the blood flow signal, the routine of removing the motion artifact and calculating the heartbeat information is terminated, and then the HRV is generated by collecting information with respect to the period determined to be the blood flow signal (S22).

Figure 7:
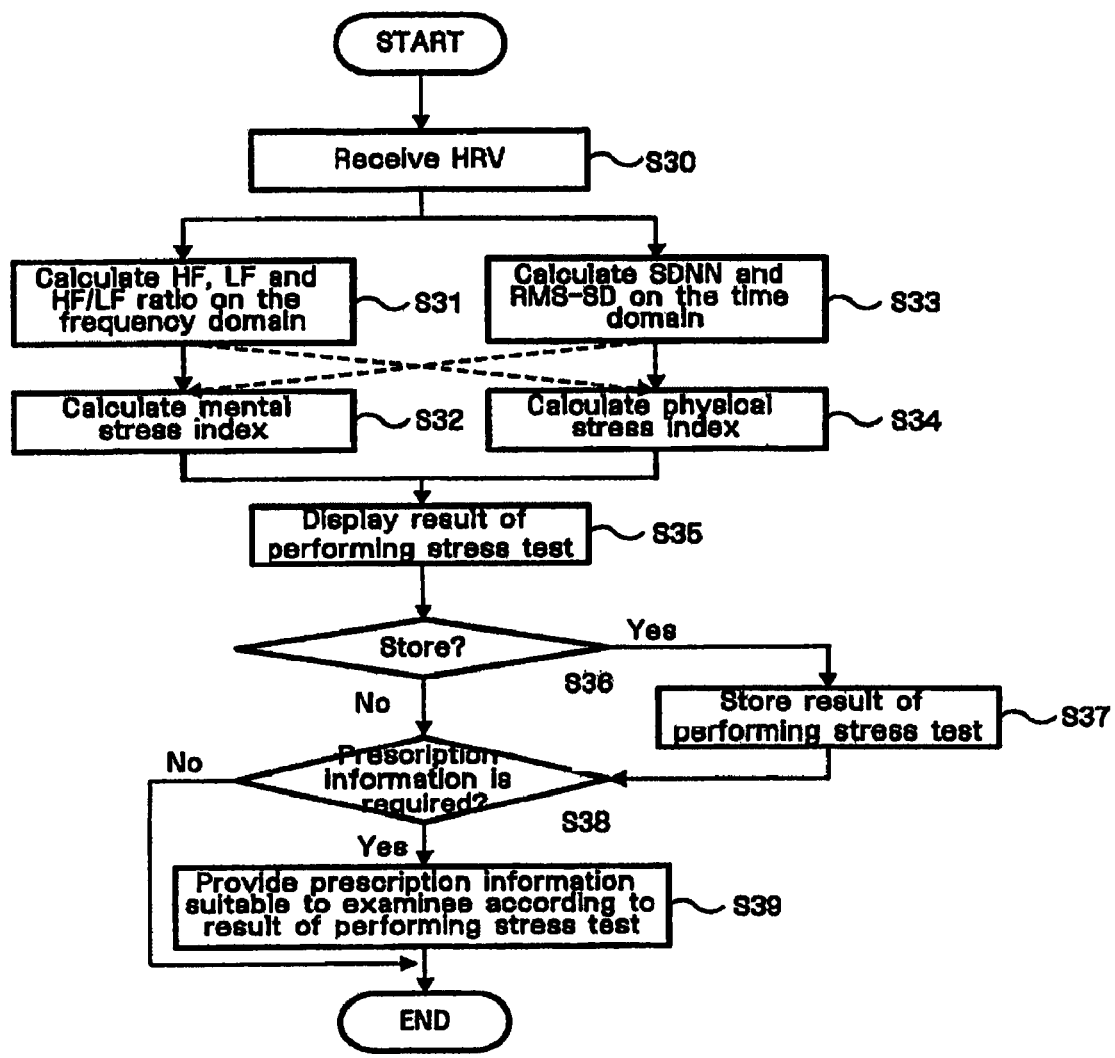
FIG. 7 is a schematic flow chart showing a procedure to perform a stress test in accordance with an embodiment of the present invention.

FIG. 7 is a schematic flow chart showing a procedure to execute a stress test in accordance with an embodiment of the invention.

As shown in FIG. 7, when receiving information on the heartbeat, such as the HR and HRV, which is processed and generated at the motion artifact removing section 310 and heartbeat information calculating section 320 (S30), the stress testing section 330 of the motion artifact removal and stress test apparatus 300 analyzes the HRV with respect to the frequency and time domains.

First, in the frequency domain of the HRV, a high frequency (HF), a low frequency (LF) and an HF/LF ratio are extracted to calculate their values (S31), and a mental stress index of the examinee is calculated by sympathetic and parasympathetic nerve indexes obtained through the calculated values of the HF, LF and HF/LF ratio (S32).

Next, the HRV is subjected to a Fourier transform, and the standard deviation of the average normal RR-intervals (referred to as SDNN hereinafter) and the root mean square of successive differences (referred to as RMS-SD hereinafter) are calculated in the time domain of the HRV (S33). A physical stress index is calculated using the calculated SDNN and RMS-SD indexes (S34).

In this manner, when the mental/physical stress indexes are calculated, the stress testing section 330 checks the current state of the examinee based on the calculated mental/physical stress indexes, and provides the result of the stress test through the display section 340 (S35).

Subsequently, the stress testing section 330 determines whether the result of the stress test provided through the display section 340 is stored according to the selection of the examinee (S36).

As a result of the determination, if the result of the stress test is stored, the result of the stress test is stored in the storage section 350 together with information on the previously registered examinee (S37). On the other hand, where desired, the result of the stress test may be omitted.

Then, the stress testing section 330 determines whether prescription information suitable for the current state of the examinee is required according to selection of the examinee (S38).

As a result of the determination, if the prescription information is required, the prescription information stored in the storage section 350 is searched for the prescription information suitable with respect to the current state of the examinee. A result of searching is provided through the display section 340. Then, the examinee selects a termination key, and thus the stress test is terminated (S39). However, if the prescription information is not required, the examinee also selects the termination key, and thus, the stress test is terminated.

Hereinafter, another method to detect a blood flow signal free from a motion artifact according to an embodiment of the invention and another method to perform a stress test using the same will be described in detail with reference to the accompanying drawings.

Figure 8:
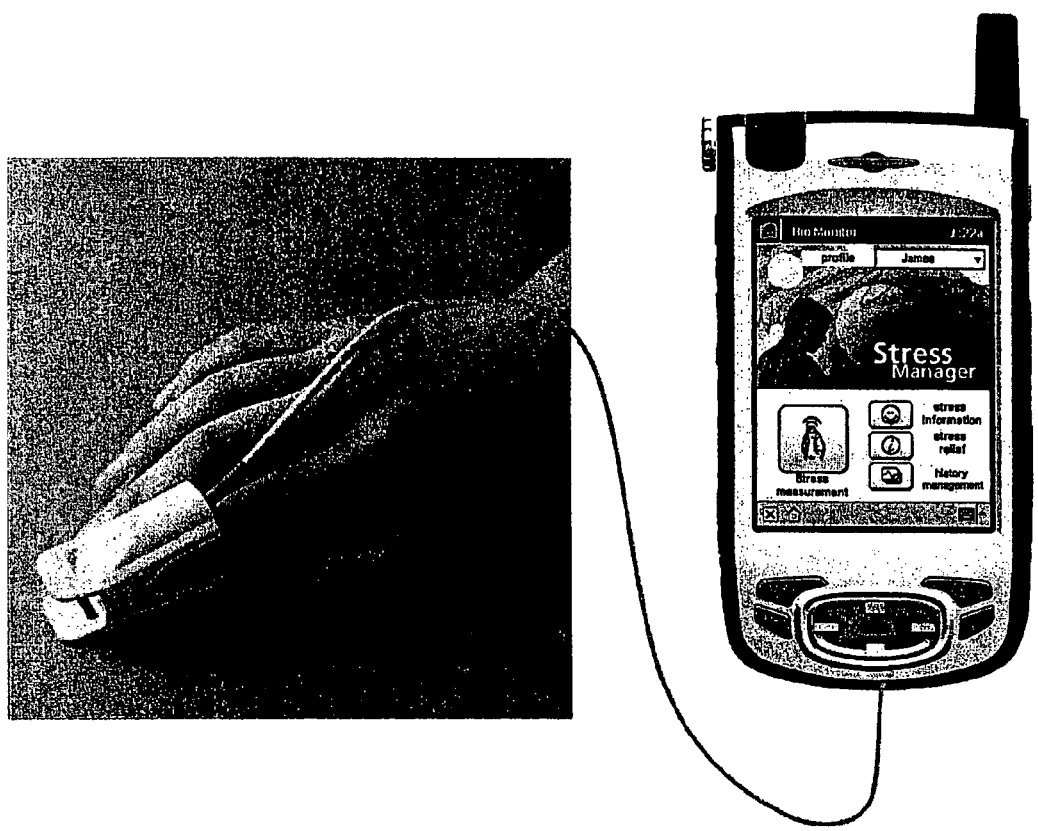
FIG. 8 shows a procedure to perform a stress test using PDA in accordance with an embodiment of the present invention.

In the case wherein an examinee, who may make use of a personal digital assistant (PDA) 500 having the motion artifact removal and stress test apparatus 300, intends to check her/his current state, the examinee, as shown in FIG. 8, fits a finger probe 700, which includes a blood flow sensing apparatus connected to the PDA 500, onto one of her/his fingers, and selects a start button for the stress test.

When the stress test is initiated according to the stress test selection of the examinee, the motion artifact removal & stress test apparatus 300 built into the PDA 500 receives a blood flow signal of the examinee which is detected through the finger probe 700.

Figure 9:
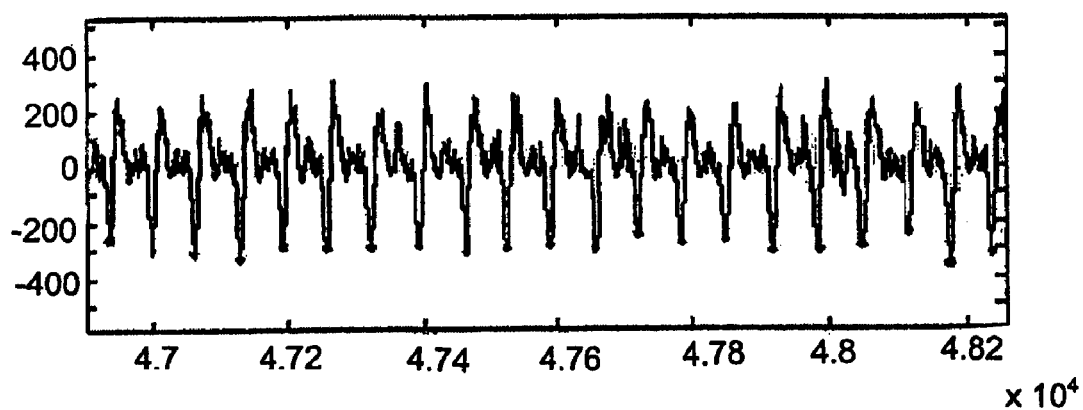
FIG. 9 shows a blood flow signal whose peak points are determined in accordance with an embodiment of the present invention.

As shown in FIG. 9, the motion artifact removing section 310 of the motion artifact removal and stress test apparatus 300 processes the received blood flow signal to remove the motion artifact, and then determines peak points.

For instance, in an example, the number of the determined peak points is 693, peak(693), and the motion artifact removing section 310 selects a first peak point R(0), and extracts the values of peak points R(0) and R(1).

Next, the motion artifact removing section 310 calculates a correlation coefficient $C_0$ at the selected pick point R(0) using Equation 1, determines whether the calculated correlation coefficient $C_0$ exceeds a threshold value of 0.8, and excludes the motion artifact from the blood flow signal as a result of the determination.

Subsequently, the heartbeat information calculating section 320 of the motion artifact removal and stress test apparatus 300 further performs the removal of the motion artifact using both the interval ΔRR between the peak points R(0) and R(1) and the HR calculated by the interval ΔRR, and determines whether R(0) is the blood flow signal.

These procedures are performed for all peak points, peak (693), of the blood flow signal, and thus the HRV derived from only the blood flow signal is generated.

Figure 10:
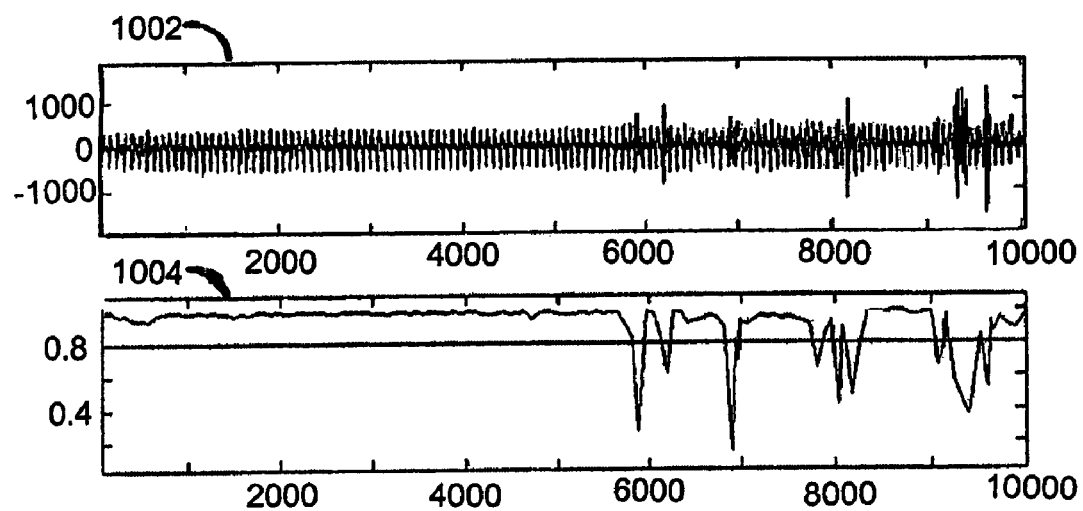
FIG. 10 shows a result of analyzing a threshold value in terms of a blood flow signal (A) in accordance with an embodiment of the present invention.

Specifically, as shown in FIG. 10, when the correlation coefficients $C_i$ are calculated at each peak point of the blood flow signal (1002), a correlation coefficient analysis result (B) is made. With use of the correlation coefficient analysis result (1004), the correlation coefficients $C_i$ are compared with the threshold value of 0.8. As a result, it may be determined whether the peak points are motion artifacts or not.

Figure 11:
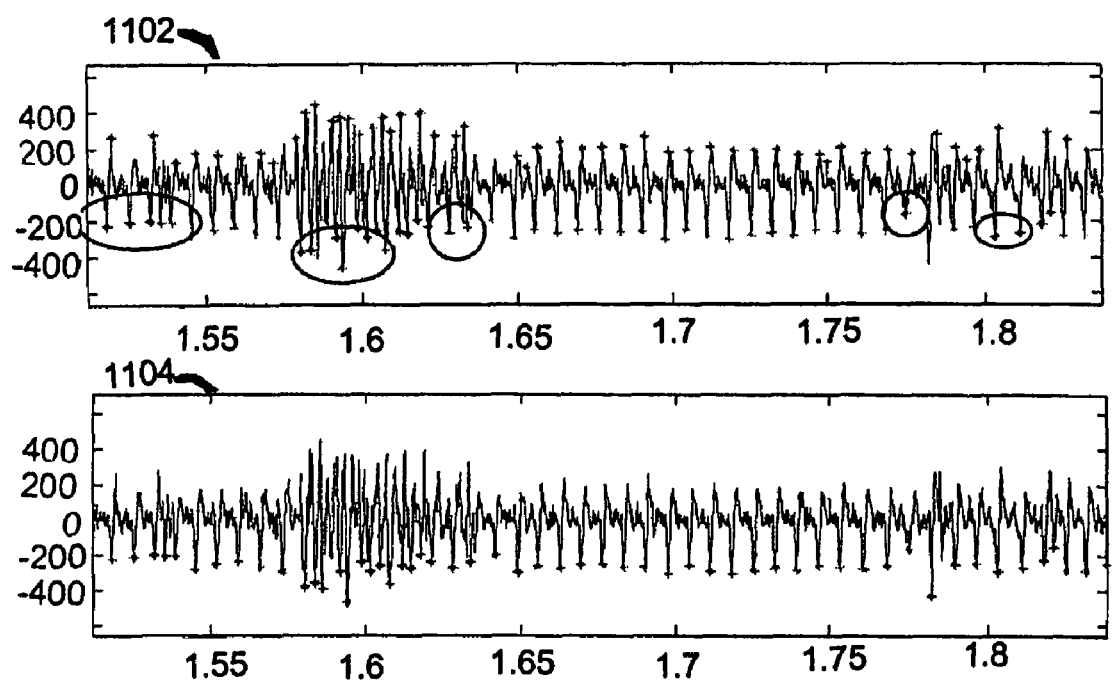
FIG. 11 shows results of determining a motion artifact in accordance with the present invention and the related art.

FIG. 11 shows results of determining a motion artifact in accordance with the invention and the related art.

In the results of FIG. 11, a red color represented at each peak point refers to the motion artifact, while a green color refers to the blood flow signal.

As shown in FIG. 11, it may be seen that, in the method of the related art (1102), the blood flow signal is frequently incorrectly determined to be a motion artifact, and vice versa.

In other words, as is shown in FIG. 11, reference numeral 1104, it may be seen that the method to detect the blood flow signal free from the motion artifact according to an embodiment of the invention determines the blood flow signal and the motion artifact signal more exactly than the method of the related art, thus enhancing the reliability of the HR calculated through the blood flow signal.

Specifically, in the total 693 motion artifact discrimination tests, the method of the invention has 10 errors, but the method of the related art has 72 errors, as indicated in the following Table 1. Thus, the method of the invention may noticeably decrease the errors according to determination of the motion artifact compared to the method of the related art.

TABLE 1

| Error type | The related art | The invention |
|---|---|---|
| Determining a blood flow signal to be a motion artifact | 47 | 9 |
| Determining a motion artifact to be a blood flow signal | 25 | 1 |
| Total | 72 | 10 |
| Error rate | 10.4% | 1.4% |

The stress testing section 330 of the motion artifact removal and stress test apparatus 300 may determine the current state of the examinee exactly through the exact HRV which is obtained by this process.

While performing the stress test, the stress testing section 330 of the motion artifact removal and stress test apparatus 300 submits a questionnaire associated with the stress test or provides animation effects through the display section 340 so that the examinee does not experience anxiety.

According to the invention, the motion artifact caused by the motion of the examinee may be effectively removed from the blood flow signal detected through the blood flow sensing apparatus, and thus, reliability of the blood flow signal is enhanced.

Also, the HR calculated using the blood flow signal free from the motion artifact may be used to test the stress state of the examinee, so that the current state of the examinee may be checked more precisely.

It should be noted that all of the above embodiments may be implemented utilizing a computer medium having computer-readable instructions stored thereon, for performing the procedures to remove the motion artifact form the blood flow signal. The present invention may be embodied as a program stored on a computer readable medium that can be run on a general computer. Here, the computer readable medium includes, but is not limited to, storage media such as magnetic storage media (e.g., ROM's, floppy disks, hard disks, and the like), optically readable media (e.g., CD-ROMs, DVDs, and the like), and carrier waves (e.g., transmission over the Internet). The present invention may also be embodied as a computer readable program code unit stored on a computer readable medium, for causing a number of computer systems connected via a network to affect distributed processing of the operations of the present invention.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An apparatus to detect a blood flow signal free from a motion artifact, comprising:
    a base pattern correlation coefficient calculating unit to determine peak points in the blood flow signal sensed from a body of an examinee, and to calculate correlation coefficients of each peak point using a predetermined base pattern; and
    a motion artifact processing unit to determine the motion artifact using the calculated correlation coefficients and to remove the motion artifact from the blood flow signal, wherein the motion artifact is determined by comparing the calculated correlation coefficients with a predetermined threshold value and determining whether the correlation coefficients are less than the predetermined threshold value.

2. The apparatus as claimed in claim 1, wherein the base pattern correlation coefficient calculating unit extracts the predetermined base pattern from a predetermined area of the blood flow signal using a degree of correlation of the calculated correlation coefficients with the predetermined base pattern, the predetermined area of the blood flow signal corresponding to an area where a pure blood flow signal is optimal, the pure blood flow signal being measured under a test environment free from the motion artifact.

3. The apparatus as claimed in claim 1, wherein the correlation coefficients are calculated using the following equation:

$$C_i = \frac{\sum_{n=0}^{N}(x_{k(i,n)} - \overline{x})(b_n - \overline{b})}{\sqrt{\sum_{n=0}^{N}(x_{k(i,n)} - \overline{x})^2 \sum_{n=0}^{N}(b_n - \overline{b})^2}}$$

$$k(i,n) = \frac{(N-n)P_i + nP_{i+1}}{N}$$

wherein where $x_n$ is an $n^{th}$ point of the blood flow signal,
$b_n$ is an $n^{th}$ point of the base pattern,
$k(i,n)$ is an $n^{th}$ point position from the $i^{th}$ peak,
$P_i$ is a $i^{th}$ peak point,
N is the number of the base pattern signal, and i and n are integers.

4. The apparatus as claimed in claim 1, wherein the predetermined threshold value has a range from 0.7 to 0.9.

5. The apparatus as claimed in claim 4, wherein the predetermined threshold value is approximately 0.8.

6. A method to detect a blood flow signal free from a motion artifact, the method comprising:
  detecting the blood flow signal sensed from a body of an examinee;
  determining peak points in the detected blood flow signal and calculating correlation coefficients of each peak point using a predetermined base pattern; and
  determining, using at least one processing device, the motion artifact using the calculated correlation coefficients and removing the motion artifact from the blood flow signal,
  wherein the determining the motion artifact using the calculated correlation coefficients compares the calculated correlation coefficients with a predetermined threshold value and determines whether the correlation coefficients are less than the predetermined threshold value.

7. The method as claimed in claim 6, wherein the base pattern correlation coefficient calculating unit extracts the predetermined base pattern from a predetermined area of the blood flow signal using a degree of correlation of the calculated correlation coefficients with the predetermined base pattern, the predetermined area of the blood flow signal corresponding to an area where a pure blood flow signal is optimal, the pure blood flow signal being measured under a test environment free from the motion artifact.

8. The method as claimed in claim 6, wherein the correlation coefficients are calculated using the following equation:

$$C_i = \frac{\sum_{n=0}^{N}(x_{k(i,n)} - \overline{x})(b_n - \overline{b})}{\sqrt{\sum_{n=0}^{N}(x_{k(i,n)} - \overline{x})^2 \sum_{n=0}^{N}(b_n - \overline{b})^2}},$$

$$k(i,n) = \frac{(N-n)P_i + nP_{i+1}}{N}$$

wherein where $x_n$ is an $n^{th}$ point of the blood flow signal,
$b_n$ is an $n^{th}$ point of the base pattern,
$k(i,n)$ is an $n^{th}$ point position from the $i^{th}$ peak,
$P_i$ is a $i^{th}$ peak point,
N is the number of the base pattern signal,
and i and n are integers.

9. The method as claimed in claim 6, wherein the predetermined threshold value has a range from 0.7 to 0.9.

10. The method as claimed in claim 9, wherein the predetermined threshold value is approximately 0.8.

11. A stress test apparatus using an apparatus to detect a blood flow signal free from a motion artifact, comprising:
  a motion artifact removing section to remove the motion artifact caused by an examinee from the blood flow signal detected from a body of the examinee;
  a heartbeat information calculating section to calculate heartbeat information using the blood flow signal from which the motion artifact is removed utilizing the motion artifact removing section; and
  a stress testing section to calculate a stress index using the heartbeat information calculated utilizing the heartbeat information calculating section and checking a physical state of the examinee,
  a base pattern correlation coefficient calculating part to determine peak points in the blood flow signal sensed from the physical state of the examinee using the blood flow sensing unit, and to calculate correlation coefficients of each peak point using a predetermined base pattern; and
  a motion artifact processing part to determine the motion artifact using the calculated correlation coefficients and to remove the motion artifact from the blood flow signal, and
  wherein the determining the motion artifact using the calculated correlation coefficients compares the calculated correlation coefficients with a predetermined threshold value and determines whether the correlation coefficients are less than the predetermined threshold value.

12. The stress test apparatus as claimed in claim 11, further comprising:
  a display section to provide information on the physical state of the examinee obtained utilizing the stress testing section on a graphic user interface (GUI) screen; and
  a storage section to store information on the physical state of the examinee and information on a suitable prescription according to the physical state of the examinee.

13. The stress test apparatus as claimed in claim 11, wherein the base pattern correlation coefficient calculating unit extracts the predetermined base pattern from a predetermined area of the blood flow signal using a degree of correlation of the calculated correlation coefficients with the predetermined base pattern, the predetermined area of the blood flow signal corresponding to an area where a pure blood flow signal is optimal, the pure blood flow signal being measured under a test environment free from the motion artifact.

14. The stress test apparatus as claimed in claim 11, wherein the correlation coefficients are calculated using the following equation:

$$C_i = \frac{\sum_{n=0}^{N}(x_{k(i,n)} - \overline{x})(b_n - \overline{b})}{\sqrt{\sum_{n=0}^{N}(x_{k(i,n)} - \overline{x})^2 \sum_{n=0}^{N}(b_n - \overline{b})^2}},$$

-continued $$k(i, n) = \frac{(N-n)P_i + nP_{i+1}}{N}$$

wherein
where $x_n$ is an $n^{th}$ point of the blood flow signal,
$b_n$ is an $n^{th}$ point of the base pattern,
k(i,n) is an $n^{th}$ point position from the $i^{th}$ peak,
$P_i$ is a $i^{th}$ peak point,
N is the number of the base pattern signal, and i and n are integers.

15. The stress test apparatus as claimed in claim 11, wherein the predetermined threshold value has a range from 0.7 to 0.9.

16. The stress test apparatus as claimed in claim 15, wherein the predetermined threshold value is approximately 0.8.

17. The stress test apparatus as claimed in claim 11, wherein the heartbeat information calculating section comprises:
 a heart rate calculating part to calculate a heart rate using an interval between peak points which are determined to be the blood flow signal utilizing the motion artifact removing section, and to determine the motion artifact by comparing the interval between the peak points with a reference range and comparing the heart rate with the reference range; and
 a heart rate variability generating part to cause removal of the motion artifact utilizing the motion artifact removing section and the heart rate calculating part that determines the heart rate at peak points of the blood flow signal, and to generate heart rate variability by collecting each peak point which is determined to be the blood flow signal.

18. The stress test apparatus as claimed in claim 11, wherein the stress index is determined by analyzing information on sympathetic and parasympathetic nerves, the information on sympathetic and parasympathetic nerves being obtained by analyzing the calculated heartbeat information using frequency and time domains.

19. A computer medium having computer-readable instructions stored thereon and executable by a computer to detect a blood flow signal free from a motion artifact, the computer-readable instructions comprising instructions for:
 using base pattern correlation coefficient calculating instructions to determine peak points in the blood flow signal sensed from a body of an examinee, and to calculate correlation coefficients of each peak point using a predetermined base pattern; and
 using motion artifact processing and the calculated correlation coefficients to determine the motion artifact and to remove the motion artifact from the blood flow signal,
 wherein the motion artifact is determined by comparing the calculated correlation coefficients with a predetermined threshold value and determining whether the correlation coefficients are less than the predetermined threshold value.

20. The computer medium as claimed in claim 19, wherein the base pattern correlation coefficient calculating unit extracts the predetermined base pattern from a predetermined area of blood flow signal using a degree of correlation of the calculated correlation coefficients with the predetermined base pattern, the predetermined area of the blood flow signal corresponding to an area where a pure blood flow signal is optimal, the pure blood flow signal being measured under a test environment free from the motion artifact.

21. The computer medium as claimed in claim 19, wherein the correlation coefficients are calculated using the following equation:

$$C_i = \frac{\sum_{n=0}^{N}(x_{k(i,n)} - \bar{x})(b_n - \bar{b})}{\sqrt{\sum_{n=0}^{N}(x_{k(i,n)} - \bar{x})^2 \sum_{n=0}^{N}(b_n - \bar{b})^2}}$$

$$k(i, n) = \frac{(N-n)P_i + nP_{i+1}}{N}$$

wherein
where $x_n$ is an $n^{th}$ point of the blood flow signal,
$b_n$ is an $n^{th}$ point of the base pattern,
k(i,n) is an $n^{th}$ point position from the $i^{th}$ peak,
$P_i$ is a $i^i$ peak point,
N is the number of the base pattern signal,
and i and n are integers.

22. The computer medium as claimed in claim 19, wherein the predetermined threshold value has a range from 0.7 to 0.9.

23. The computer medium as claimed in claim 22, wherein the predetermined threshold value is approximately 0.8.

24. A computer medium having computer-readable instructions stored thereon and executable by a computer to detect a blood flow signal free from a motion artifact, the computer-readable instructions comprising instructions for performing:
 detecting the blood flow signal sensed from a body of an examinee;
 determining peak points in the detected blood flow signal and calculating correlation coefficients of each peak point using a predetermined base pattern; and
 determining the motion artifact using the calculated correlation coefficients and removing the motion artifact from the blood flow signal,
 wherein the determining the motion artifact using the calculated correlation coefficients compares the calculated correlation coefficients with a predetermined threshold value and determines whether the correlation coefficients are less than the predetermined threshold value.

25. The computer medium as claimed in claim 24, wherein the base pattern correlation coefficient calculating unit extracts the predetermined base pattern from a predetermined area of the blood flow signal using a degree of correlation of the calculated correlation coefficients with the predetermined base pattern, the predetermined area of the blood flow signal corresponding to an area where a pure blood flow signal is optimal, the pure blood flow signal being measured under a test environment free from the motion artifact.

26. The computer medium as claimed in claim 24, wherein the correlation coefficients are calculated using the following equation:

$$C_i = \frac{\sum_{n=0}^{N}(x_{k(i,n)} - \bar{x})(b_n - \bar{b})}{\sqrt{\sum_{n=0}^{N}(x_{k(i,n)} - \bar{x})^2 \sum_{n=0}^{N}(b_n - \bar{b})^2}},$$

-continued $$k(i, n) = \frac{(N-n)P_i + nP_{i+1}}{N}$$

wherein where $x_n$ is an $n^{th}$ point of the blood flow signal, $b_n$ is an $n^{th}$ point of the base pattern, $k(i,n)$ is an nth point position from the $i^{th}$ peak, $P_i$ is a $i^{th}$ peak point, N is the number of the base pattern signal, and i and n are integers.

27. The computer medium as claimed in claim 24, wherein the predetermined threshold value has a range from 0.7 to 0.9.

28. The computer medium as claimed in claim 27, wherein the predetermined threshold value is approximately 0.8.

29. A computer medium having computer-readable instructions stored thereon and executable by a computer to detect a blood flow signal free from a motion artifact, the computer-readable instructions comprising instructions for:

removing the motion artifact caused by an examinee from the blood flow signal detected from a body of the examinee;

calculating heartbeat information using the blood flow signal from which the motion artifact is removed; and calculating a stress index using both the heartbeat information and information on a physical state of the examinee, calculating a base pattern correlation coefficient to determine peak points in the blood flow signal sensed from the physical state of the examinee, and calculating correlation coefficients of each peak point using a predetermined base pattern; and using motion artifact processing to determine the motion artifact using the calculated correlation coefficients and removing the motion artifact from the blood flow signal, wherein the determining the motion artifact using the calculated correlation coefficients compares the calculated correlation coefficients with a predetermined threshold value and determines whether the correlation coefficients are less than the predetermined threshold value.

30. The computer medium as claimed in claim 29, further comprising instructions for:

providing information on the physical state of the examinee on a graphic user interface (GUI) screen; and storing information on the physical state of the examinee and information on a suitable prescription according to the physical state of the examinee.

31. The computer medium as claimed in claim 29, wherein the base pattern correlation coefficient calculating unit extracts the predetermined base pattern from a predetermined area of the blood flow signal using a degree of correlation of the calculated correlation coefficients with the predetermined base pattern, the predetermined area of the blood flow signal corresponding to an area where a pure blood flow signal is optimal, the pure blood flow signal being measured under a test environment free from the motion artifact.

32. The computer medium as claimed in claim 29, wherein the correlation coefficients are calculated using the following equation:

$$C_i = \frac{\sum_{n=0}^{N}(x_{k(i,n)} - \overline{x})(b_n - \overline{b})}{\sqrt{\sum_{n=0}^{N}(x_{k(i,n)} - \overline{x})^2 \sum_{n=0}^{N}(b_n - \overline{b})^2}},$$

$$k(i, n) = \frac{(N-n)P_i + nP_{i+1}}{N}$$

wherein where $x_n$ is an $n^{th}$ point of the blood flow signal, $b_n$ is an $n^{th}$ point of the base pattern, $k(i,n)$ is an $n^{th}$ point position from the $i^{th}$ peak, $P_i$, is a $i^{th}$ peak point, N is the number of the base pattern signal, and i and n are integers.

33. The computer medium as claimed in claim 29, wherein the predetermined threshold value has a range from 0.7 to 0.9.

34. The computer medium as claimed in claim 33, wherein the predetermined threshold value is approximately 0.8.

35. The computer medium as claimed in claim 29, wherein the calculating the heartbeat information comprises:

calculating a heart rate using an interval between the peak points which are determined to be the blood flow signal, and determining the motion artifact by comparing the interval between the peak points with a reference range and comparing the heart rate with the reference range; and removing the motion artifact using the heart rate calculated at peak points of the blood flow signal, and generating a heart rate variability by collecting each peak point which is determined to be the blood flow signal.

36. The computer medium as claimed in claim 29, wherein the stress index is determined by analyzing information on sympathetic and parasympathetic nerves, the information on sympathetic and parasympathetic nerves being obtained by analyzing the calculated heartbeat information using frequency and time domains.

37. An apparatus to remove a motion artifact from a filtered blood flow signal, wherein the filtered blood flow signal has been filtered to obtain waveforms of a predetermined frequency band, the apparatus comprising:

a base pattern correlation coefficient calculating unit to determine peak points in the waveforms of the predetermined frequency band, and to calculate correlation coefficients of each peak point using a predetermined base pattern; and a motion artifact processing unit to determine the motion artifact using the calculated correlation coefficients and to remove the motion artifact from the blood flow signal, wherein the motion artifact is determined by comparing the calculated correlation coefficients with a predetermined threshold value and determining whether the correlation coefficients are less than the predetermined threshold value.

38. The apparatus as claimed in claim 37, wherein the base pattern correlation coefficient calculating unit extracts the predetermined base pattern from a predetermined area of the blood flow signal using a degree of correlation of the calculated correlation coefficients with the predetermined base pattern, the predetermined area of the blood flow signal corresponding to an area where a pure blood flow signal is optimal, the pure blood flow signal being measured under a test environment free from the motion artifact.

39. The apparatus as claimed in claim 37, wherein the correlation coefficients are calculated using the following equation:

$$C_i = \frac{\sum_{n=0}^{N}(x_{k(i,n)} - \bar{x})(b_n - \bar{b})}{\sqrt{\sum_{n=0}^{N}(x_{k(i,n)} - \bar{x})^2 \sum_{n=0}^{N}(b_n - \bar{b})^2}},$$

$$k(i,n) = \frac{(N-n)P_i + nP_{i+1}}{N}$$

wherein where $x_n$ is an $n^{th}$ point of the blood flow signal, $b_n$ is an $n^{th}$ point of the base pattern, k(i,n) is an $n^{th}$ point position from the $i^{th}$ peak, $P_i$, is a $i^{th}$ peak point, N is the number of the base pattern signal, and i and n are integers.

40. The apparatus as claimed in claim 37, wherein the predetermined threshold value has a range from 0.7 to 0.9.

41. The apparatus as claimed in claim 4, wherein the predetermined threshold value is approximately 0.8.

* * * * *

UNITED STATES PATENT AND TRADEMARK OFFICE
CERTIFICATE OF CORRECTION

PATENT NO. : 7,727,159 B2
APPLICATION NO. : 10/909305
DATED : June 1, 2010
INVENTOR(S) : Ki-wan Choi et al.

It is certified that error appears in the above-identified patent and that said Letters Patent is hereby corrected as shown below:

Column 11, Lines 6-16 (Approx.) in Claim 3, delete

"
$$C_i = \frac{\sum_{n=0}^{N}(x_{k(i,n)} - \bar{x})(b_n - \bar{b})}{\sqrt{\sum_{n=0}^{N}(x_{k(i,n)} - \bar{x})^2 \sum_{n=0}^{N}(b_n - \bar{b})^2}}$$

$$k(i,n) = \frac{(N-n)P_i + nP_{i+1}}{N}$$
" and insert

"
$$C_i = \frac{\sum_{n=0}^{N}(x_{k(i,n)} - \bar{x})(b_n - \bar{b})}{\sqrt{\sum_{n=0}^{N}(x_{k(i,n)} - \bar{x})^2 \sum_{n=0}^{N}(b_n - \bar{b})^2}}$$

$$k(i,n) = \frac{(N-n)P_i + nP_{i+1}}{N}$$
, --.

Column 11, Line 64 delete

" $k(i,n) = \frac{(N-n)P_i + nP_{i+1}}{N}$ " and insert the same after wherein in Column 12, Line 1.

Signed and Sealed this
Twelfth Day of June, 2012

David J. Kappos
*Director of the United States Patent and Trademark Office*

CERTIFICATE OF CORRECTION (continued)
U.S. Pat. No. 7,727,159 B2

Column 13, Lines 3-7 in Claim 14, delete

" $k(i,n) = \dfrac{(N-n)P_i + nP_{i+1}}{N}$ " and insert

-- $k(i,n) = \dfrac{(N-n)P_i + nP_{i+1}}{N}$ , --.

Column 14, Lines 9-18 in Claim 21, delete

" $C_i = \dfrac{\sum\limits_{n=0}^{N}(x_{k(i,n)} - \bar{x})(b_n - \bar{b})}{\sqrt{\sum\limits_{n=0}^{N}(x_{k(i,n)} - \bar{x})^2 \sum\limits_{n=0}^{N}(b_n - \bar{b})^2}}$ $k(i,n) = \dfrac{(N-n)P_i + nP_{i+1}}{N}$ " and insert -- $C_i = \dfrac{\sum\limits_{n=0}^{N}(x_{k(i,n)} - \bar{x})(b_n - \bar{b})}{\sqrt{\sum\limits_{n=0}^{N}(x_{k(i,n)} - \bar{x})^2 \sum\limits_{n=0}^{N}(b_n - \bar{b})^2}}$ $k(i,n) = \dfrac{(N-n)P_i + nP_{i+1}}{N}$ , --.

Column 14, Line 22 in Claim 21, delete "i'" and insert -- $i^{th}$ --.

Column 15, Lines 3-7 in Claim 26, delete "wherein $k(i,n) = \dfrac{(N-n)P_i + nP_{i+1}}{N}$ " and insert -- wherein $k(i,n) = \dfrac{(N-n)P_i + nP_{i+1}}{N}$ , --.

Column 15, Line 11 in Claim 26, delete "nth" and insert -- $n^{th}$ --.

CERTIFICATE OF CORRECTION (continued)
U.S. Pat. No. 7,727,159 B2

Column 16, Lines 10-13 in Claim 32, delete "wherein $k(i,n) = \dfrac{(N-n)P_i + nP_{i+1}}{N}$ " and insert -- wherein $k(i,n) = \dfrac{(N-n)P_i + nP_{i+1}}{N}$ , --.

Column 16, Line 17 in Claim 32, delete "P$_i$," and insert -- P$_i$ --.

Columns 17, Lines 12-13 delete " $k(i,n) = \dfrac{(N-n)P_i + nP_{i+1}}{N}$ " and insert -- $k(i,n) = \dfrac{(N-n)P_i + nP_{i+1}}{N}$ -- after wherein in Column 18, Claim 39.

Column 18, Line 6 in Claim 39, delete "Pi," and insert -- Pi --.